United States Patent
Michl et al.

(10) Patent No.: US 7,288,675 B2
(45) Date of Patent: Oct. 30, 2007

(54) METHOD AND DEVICE FOR HYDROLYTICALLY OBTAINING A CARBOXYLIC ACID AND ALCOHOL FROM THE CORRESPONDING CARBOXYLIC ESTER

(75) Inventors: Harald Michl, Kastl (DE); Franz Ramgraber, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 10/536,689

(22) PCT Filed: Nov. 27, 2003

(86) PCT No.: PCT/EP03/13384

§ 371 (c)(1),
(2), (4) Date: Jan. 12, 2006

(87) PCT Pub. No.: WO2004/048308

PCT Pub. Date: Jun. 10, 2004

(65) Prior Publication Data

US 2006/0128991 A1    Jun. 15, 2006

(30) Foreign Application Priority Data

Nov. 28, 2002   (DE) ................. 102 55 648

(51) Int. Cl.
*C07C 53/00* (2006.01)
*C07C 53/08* (2006.01)
(52) U.S. Cl. .................................... 562/606; 562/607
(58) Field of Classification Search ................... None
See application file for complete search history.

(56) References Cited

U.S. PATENT DOCUMENTS

| 4,352,940 | A | 10/1982 | Adelman |
| 5,113,015 | A | 5/1992 | Palmer et al. |
| 5,417,939 | A | 5/1995 | Bunschoten et al. |
| 5,470,542 | A | 11/1995 | Stringaro |
| 5,536,699 | A | 7/1996 | Ghelfi et al. |
| 5,770,770 | A | 6/1998 | Kim et al. |

FOREIGN PATENT DOCUMENTS

| EP | 1 220 825 | 5/2003 |
| WO | WO 0127062 | 4/2001 |

*Primary Examiner*—Paul A. Zucker
(74) *Attorney, Agent, or Firm*—Brooks Kushman P.C.

(57) ABSTRACT

A process and apparatus for hydrolytic cleavage of carboxylic esters and water into carboxylic acid and alcohol hydrolysis products. In the process, a portion of water required for hydrolysis is replaced by a recycled mixture of carboxylic acid and water from previously hydrolyzed carboxylic ester.

10 Claims, 5 Drawing Sheets

METHOD AND DEVICE FOR HYDROLYTICALLY OBTAINING A CARBOXYLIC ACID AND ALCOHOL FROM THE CORRESPONDING CARBOXYLIC ESTER

CROSS-REFERENCE TO RELATED APPLICATION

This application claims priority to PCT Appln. No. PCT/US03/013384 filed Nov. 27, 2003, and to German application 102 55 648.2 filed Nov. 28, 2002.

BACKGROUND OF THE INVENTION

1. Field of the Invention

The present invention relates to a process, and also to an apparatus, for improved hydrolytic cleavage of carboxylic esters to the corresponding carboxylic acid and alcohol, in which at least a portion of the water required for hydrolysis is replaced by a recycled mixture comprising carboxylic acid and water which results from the hydrolysis of carboxylic ester already converted in the process.

2. Description of the Related Art

The inverse of esterification is the hydrolysis of the carboxylic ester to carboxylic acid and alcohol. Like the esterification itself, the acid-catalyzed hydrolysis is an equilibrium reaction. Carboxylic esters are used in the chemical industry, for example, as solvents or plasticizers, or are obtained in various reactions as by-products or main products. For example, methyl acetate is a typical by-product in the preparation of polyvinyl alcohol. Mixtures comprising methyl acetate which are obtained in the preparation of polyvinyl alcohol, in addition to a small amount of low-boiling substances, for example acetaldehyde, comprise an azeotropic mixture of methyl acetate and methanol. Mixtures of the composition described can be economically utilized only with difficulty, if at all, without further purification or cleavage (hydrolysis) of the carboxylic esters to the reactants.

The hydrolysis of carboxylic esters can be carried out batchwise or continuously. Suitable for this purpose is a reactor in combination with a conventional distillation or a reactive distillation column. The use of a reactor in combination with a distillation column for the hydrolysis of methyl acetate is described, for example, in the patent U.S. Pat. No. 4,352,940. The process described there for hydrolyzing methyl acetate is disadvantageous, among other reasons, because the yields are small and a plurality of distillation stages is necessary. In addition, corrosion occurs as a result of the use of sulfuric acid or hydrochloric acid as homogeneous catalysts.

The patent specification U.S. Pat. No. 5,113,015 describes a process for hydrolyzing methyl acetate, in which methyl acetate and water are contacted with a catalyst packing in a distillation column, which hydrolyzes methyl acetate to acetic acid and methanol and at the same time at least partially separates the reaction mixture in the separating column.

The patent specification U.S. Pat. No. 5,770,770 likewise discloses a process for hydrolyzing a methyl acetate mixture in a reactive distillation column, in which the hydrolysis of a methyl acetate stream containing at least 50% by weight of methyl acetate takes place in a reaction zone having an ion exchanger packing. The methyl acetate mixture and water are conducted in countercurrent over the ion exchanger packing. Unconverted methyl acetate and water are recycled into the reaction zone. The hydrolysis products are removed from the bottom fraction. The impurities are recycled back into the reaction zone.

The teachings of the patents U.S. Pat. No. 5,113,015 and U.S. Pat. No. 5,770,770 is the use of strongly acidic ion exchangers as catalysts for the hydrolysis of carboxylic esters. The patent U.S. Pat. No. 5,770,770 further describes the use of the ion exchanger material preferably in the form of Raschig rings, whereas, in U.S. Pat. No. 5,113,015, the catalyst material is preferably used in the form of mats. The catalyst packing material used may be pliable, open-meshed substances, for example wire mesh, rigid, cellular monoliths of steel, polymers or ceramic material, and also corrugated metal, plastics or ceramic plates.

The last few processes described which use only a single reactive distillation column have the disadvantage that methyl acetate is only partly hydrolyzed. The reactant stream makes necessary the use of at least one additional purification stage. It is also disadvantageous that metal ions from the methyl acetate feed deactivate the catalyst in the reactive distillation column, which leads to short on-stream times of such continuous plants.

The European laid-open specification EP 1 220 825 A2 describes a process in which the feed stream comprising the carboxylic ester is fed into a prereactor in which the carboxylic ester is contacted with a first catalyst in the presence of water, which partly hydrolyzes the carboxylic ester to the hydrolysis products. The reaction mixture from the prereactor is passed into a reactive distillation column and is contacted with a second hydrolysis catalyst for the purpose of at least partial conversion of the remaining carboxylic ester to the corresponding carboxylic acid and alcohol.

The process described in EP 1 220 825 has the advantage that a higher conversion rate can be attained than in the aforementioned processes. In addition, the use of a prereactor improves the on-stream time of the reactive distillation column, since catalyst poisons, for example metal ions, remain principally in the prereactor. The selection of the particle size of the catalyst material used in the prereactor is less restricted than for the structured catalyst packings used advantageously in the reactive distillation column.

Even when there is initial increased recycling of methyl acetate-rich top stream of the reactive distillation column to the prereactor, the capacity using an existing structure is limited as a consequence of the fixed geometry of the reaction part of the reactive distillation column.

The process described in EP 1 220 825 also has the disadvantage that, when the feed stream of carboxylic ester comprises the corresponding alcohol, the chemical equilibrium of the acid-catalyzed hydrolysis is shifted unfavourably for the products in the reaction part of the reactive distillation column.

SUMMARY OF THE INVENTION

The present invention has the object of providing an improved process and also an apparatus for acid-catalyzed hydrolysis of carboxylic esters by means of a reactive distillation column. It is a further aim of this invention to attain high conversion rates of carboxylic esters to alcohol and carboxylic acid with simultaneous use of mixtures of the carboxylic ester with the corresponding alcohol in variable compositions.

The object of this invention is achieved by a process for acid-catalyzed hydrolysis of a carboxylic ester to the corresponding carboxylic acid and the corresponding alcohol in the presence of water by passing an inlet stream comprising the carboxylic ester mixed with water into a first prereactor having a hydrolysis catalyst, which hydrolyzes the carboxylic ester at least partly to the hydrolysis products, removing the reaction mixture from this first prereactor and passing it at least partly into a reactive distillation column comprising a hydrolysis catalyst, which converts the carboxylic ester stream comprising water further to carboxylic acid and alcohol and simultaneously at least partly separates it into the components, the mixtures comprising the less volatile compounds and the low-boiling carboxylic esters being removed at least partly as a distillate, for example as a top fraction, and the less volatile compounds collecting at least partly as a bottom fraction which is passed into a further distillation column, which comprises feeding the aqueous carboxylic acid from the bottom fraction or from the lower rectification zone on the distillation column, mixed with further carboxylic ester, to a second prereactor comprising a hydrolysis catalyst, removing the reaction mixture from the second prereactor and passing it at least partly into the reactive distillation column.

DETAILED DESCRIPTION OF THE PREFERRED EMBODIMENT(S)

Figure 1:
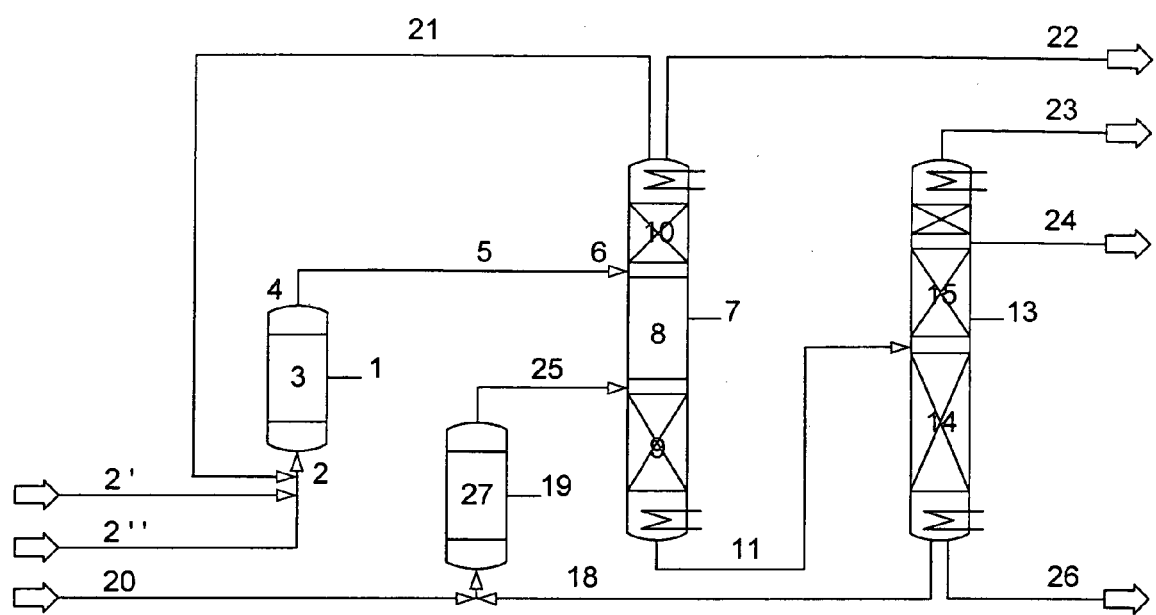
FIG. 1 illustrates one embodiment of the present process and apparatus.

In this context, the distillate of the reactive distillation column is defined as every fraction withdrawn from the distillation column above the reaction zone, including the entire condensation system of the reactive distillation column, for example a sidestream or a fraction withdrawn by partial condensation, a substream or the entire top fraction or else fractions thereof.

Advantageously, at least a portion of the bottom fraction of the reactive distillation column is fed to at least one further distillation column and is separated at least partly into the components. Preference is given to using one or more downstream separating stages when the resulting reaction mixture is to be separated into the individual components. The bottom fraction or a fraction from the lower rectification zone, preferably a fraction from the lower half of the rectification zone of this distillation column, comprising the resulting carboxylic acid and water, is fed at least partly to the second prereactor, in which case it can be mixed beforehand with the new carboxylic ester feed or with the distillate of the reactive distillation column which occurs directly or has been concentrated in carboxylic ester by means of further separating steps and comprises carboxylic ester which is yet to be converted and was originally fed to the inlet of the first prereactor.

When mixing the aqueous carboxylic acid from the bottom fraction of the distillation column or a fraction from the lower rectification zone, it is advantageous that this stream already has an elevated temperature of from 50 to 150° C., and when mixing with the stream comprising carboxylic ester for entry into the second prereactor, the resulting mixture heats to temperatures of from 50 to 100° C. It is therefore not necessary to again feed energy to the process in the form of heat to heat the feed of the second prereactor.

The carboxylic ester stream for the overall process, which is fed to one or both prereactors, is advantageously mixed with at least an equimolar amount of water. The molar ratio between carboxylic ester and water is appropriately between 1:1 and 1:15, preferably between 1:2 and 1:10 and more preferably between 1:4 and 1:8.

The hydrolysis reaction can also be carried out at room temperature. Preference is given to heating the mixture of carboxylic ester and water to a temperature between 30 and 120° C., more preferably to from 50 to 100° C., since the hydrolysis equilibrium is shifted at elevated temperatures advantageously to the side of the carboxylic acid and alcohol products, and the reaction rate is increased. The selection of the temperature is characterized substantially by the thermal stability of the ion exchanger.

The reactive distillation column is particularly advantageously operated in such a way that the carboxylic acid and at least a portion of the water and of the alcohol remain in the bottom fraction of the reactive distillation column. In this case, the reaction mixture from the first prereactor is introduced into the reactive distillation column, preferably into the reactive distillation column at a point in the upper third of the catalyst zone or above the catalyst zone and below the upper rectification zone. In the case of the hydrolysis of relatively high-boiling carboxylic acids which form a low-boiling, water-rich, usually ternary, azeotrope, for example isobutyl acetate, it is advantageous to feed it in at a point below the reaction zone and above the lower rectification zone or in the upper third of the lower rectification zone. The reaction mixture from the second prereactor is advantageously fed in below the reaction zone and above the lower rectification zone, or in the case of the hydrolysis of relatively high-boiling carboxylic acids which form a water-rich, usually ternary azeotrope, advantageously into the upper third of the lower rectification zone. The bottom fraction which occurs and comprises, for example, alcohol, water and carboxylic acid is fed to a further distillation column in which the mixture is separated further.

The distillate of the reactive distillation column, directly or after passing through further separation or distillation stages, can be fed partly to the first prereactor, to the second prereactor or both prereactors, in order to further convert any carboxylic ester still present in the distillate. Such recycling of the distillate of the reactive distillation column allows the capacity of the plant to be substantially increased.

As a consequence of the typically rising content of low-boiling impurities which are at least partly discharged at the top of the reactive distillation column, and of the water content rising toward the catalyst zone in the case of a feed, which is preferably disposed above the catalyst zone, into the reactive distillation column, it is advantageous to withdraw the distillate from the upper rectification zone which is preferably disposed above the catalyst zone, preferably in its lower third.

The process according to the invention is preferably operated continuously, i.e. carboxylic ester and water are passed continuously into the first prereactor and the resulting reaction mixture is removed continuously from the first prereactor and passed into the reactive distillation column in which unconverted carboxylic ester is for the most part converted to its hydrolysis products. In the continuous process, the hydrolysis products are removed continuously in the distillate, in the top fraction and in the bottom fraction, and, preferably, the distillate, directly or after passing through further separation or distillation stages to concentrate the carboxylic ester, is continuously fed back to the first prereactor, to the second prereactor, or to both prereactors, the bottom fraction is likewise fed continuously to a distillation column and the aqueous carboxylic acid in the bottom fraction or a fraction from the lower rectification zone, preferably from the lower half of the lower rectification zone, of this distillation column is fed at least partly, mixed with carboxylic ester, to the second prereactor. The volume stream fed per unit volume of hydrolysis catalyst in both prereactors is advantageously between 0.1-15 $h^{-1}$, preferably 0.5-8 $h^{-1}$ and more preferably between 1-4 $h^{-1}$.

The present invention also provides an apparatus for acid-catalyzed hydrolysis of a carboxylic ester to the corresponding carboxylic acid and the corresponding alcohol in the presence of water, comprising a) a first prereactor 1 comprising a hydrolysis catalyst and having at least one inlet line 2 for feeding in a fluid stream comprising the carboxylic ester, line 2', and water, line 2", and also at least one outlet 4 for removing the reaction mixture, b) at least one heating apparatus for heating the inlet stream, line 2, of the first prereactor 1, or both, c) a second prereactor 19 comprising a hydrolysis catalyst and having at least one inlet for a fluid stream comprising at least partly the aqueous carboxylic acid from the bottom fraction or a fraction of the lower rectification zone 14 of the distillation column 13, line 18, also mixed with a carboxylic ester stream, line 20, and at least one outlet, line 25, d) a reactive distillation column 7 comprising a catalyst zone 8 having a hydrolysis catalyst and having an inlet 6 connected to the first prereactor 1, an inlet connected to the second prereactor, line 25, the catalyst zone 8 being disposed between a lower rectification zone 9 and an upper rectification zone 10, e) line 22 attached at the distillation head or at the condensation system of the reactive distillation column for removing the top fraction or as a purge, f) line 21 connecting to the line 22 conducting the top fraction of the reactive distillation column 7 or connecting to the upper distillation part 10 including the entire condensation system of the reactive distillation column 7, for removing distillate, g) line 11 attached at the distillation bottom of the reactive distillation column 7, for removing the bottom fraction, h) a distillation column 13, the line 11 forming the inlet for removing the bottom fraction of the reactive distillation column 7, at whose distillation bottom, line 26, aqueous carboxylic acid is removed, i) line 18 conducting a fraction of aqueous carboxylic acid withdrawn from the lower rectification zone 14 of the distillation column 13 or a portion of line 26, this forming the inlet to the second prereactor 19, mixed with the carboxylic ester, line 20.

In a preferred embodiment, the first or second prereactor independently has two reaction chambers. In addition, means may be provided to be able to pass the feed stream in each case through one of the reaction chambers, so that the other reaction chamber in each case can be charged with fresh catalyst. This has the advantage that the equipment can be operated continuously over a long period. In a further preferred embodiment, the first or second prereactor independently has a bypass, in order to likewise ensure the exchange of the structured catalyst packing without interrupting the continuous operation of the apparatus.

The reactive distillation column 7 preferably has a catalyst zone 8 and also a lower (9) and an upper rectification zone 10, and the catalyst zone 8 is disposed between the lower and the upper rectification zone (9,10). The rectification zones may have separating trays, Raschig rings, structured mass transfer packings or the like.

The first prereactor 1, the second prereactor 19 or the reactive distillation column 7 are advantageously each independently configured as a tube. In this tube, a hydrolysis catalyst can be charged in a random manner or arranged in a structured catalyst packing. The hydrolysis catalysts are appropriately acidic solid catalysts, preferably having a particle size of between about 0.3 and 3 mm, with preference between 0.6 and 1.2 mm. While the hydrolysis catalysts in the prereactors (1, 19) are preferably in the form of spheres, rings, extrudates, etc., as a random packing, the hydrolysis catalyst of the reactive distillation column 7 is advantageously installed as a structured catalyst packing. Suitable structured catalyst packings are described, for example, in the patent specifications U.S. Pat. No. 5,417,939, U.S. Pat. No. 5,470,542 and U.S. Pat. No. 5,536,699, whose disclosure contents on this subject is incorporated herein by reference. In this context, a structured catalyst packing is a structure having retaining features (e.g. pockets) for solid catalyst material and having flow channels which are provided in the structure. It is also conceivable to use such structured catalyst packings both in the prereactors (1, 19) and in the reactive distillation column 7. The prereactors (1, 19) may also, for example, be configured in the form of stirrers having installed or fluidized catalyst. The reactive distillation column 7 selected may be a tray column, and the ion exchanger as the catalyst may be disposed on the trays themselves and in the downcomers.

In a further preferred embodiment, the inlet line 2 to the first prereactor is heated by mixing the carboxylic ester stream, line 2', with hot water, line 2", for example heating vapor condensate, in order to thus set the desired reaction temperature. In this preferred embodiment, a further heating apparatus of the feed of the first prereactor and also of the prereactor itself can be dispensed with.

FIG. 1 shows a schematic illustration of a preferred embodiment of the inventive apparatus. The first prereactor 1 has an inlet line 2 for introducing a fluid stream into the reactor chamber 3 containing the hydrolysis catalyst, preferably an acidic solid catalyst, and an outlet 4, for removing the reaction mixture. The connecting line 5 connects the outlet 4 of the first prereactor to an inlet 6 to the reactive distillation column 7. The first prereactor 1 is preferably tubular, and the inlet line 2 is supplied from the feed of the carboxylic ester mixture to be hydrolyzed, line 2', and the feed of the water, line 2". The first prereactor 1 has a hydrolysis catalyst which is disposed in the reactor chamber 3.

The reactive distillation column 7 has a catalyst zone 8 and a lower rectification zone 9 and also an upper rectification zone 10 which are arranged below and above the catalyst zone 8 respectively. The catalyst zone 8 contains a hydrolysis catalyst, preferably an acidic solid catalyst, more preferably in a structured catalyst packing. The rectification zones are formed, for example, by Raschig rings, column trays, structured (mass transfer) packings or the like in a known manner. At the bottom of the column of the lower rectification zone 9, a line 11 is provided for removing the bottom fraction and, at the top of the column of the upper rectification zone 10, a line 22 is provided for removing the top fraction of the reactive distillation column 7. The feed of the products of the first prereactor 1, line 5, is preferably above the reaction zone 8 and below the upper rectification zone 10 or in the upper third of the reaction zone 8. In the case of higher-boiling carboxylic esters which form a low-boiling, water-rich, usually ternary, azeotrope, it is advantageous to feed in below the reaction zone 8 and above the upper rectification zone 9 or in the upper third of the lower rectification zone 9.

The line 11 is connected to a distillation column 13. The distillation column 13 preferably has a lower rectification zone 14 and an upper rectification zone 15. The line 11 is preferably attached between the rectification zones 14 and 15 of the distillation column 13. The reaction product withdrawn from the distillation column 13 is aqueous carboxylic acid as the bottom fraction which is removed via line 26. A portion of the aqueous carboxylic acid is withdrawn either from line 26, the bottom of the distillation column 13, or from the lower rectification zone 14, preferably the lower half of the lower rectification zone 14, and at least partly fed to the second prereactor 19 via line 18. Upstream of entry into the second prereactor 19 having the reaction chamber 27 filled with hydrolysis catalyst, preferably an acidic solid catalyst, further carboxylic ester is fed to line 18 via line 20.

The second prereactor has a catalyst zone 27 which preferably contains an acidic solid catalyst. The second prereactor is preferably flowed through from bottom to top. The outlet of the second prereactor is connected to the reactive distillation column 7 by means of the line 25. The line 25 is preferably conducted into the reactive distillation column 7 below the catalyst zone 8 and above the lower rectification zone 9. In the case of the hydrolysis of relatively high-boiling carboxylic esters having a high water content in the ternary azeotrope, the feed from the second prereactor into the hydrolysis column can optionally be optimized by passing it into the upper third of the lower rectification column 9.

The line 22 for removing the top fraction of the reactive distillation column 7 comprising unconverted carboxylic ester can be connected via line 21 to line 2, line 2' or line 2" of the carboxylic ester mixture to be hydrolyzed. A portion of the top fraction of the reactive distillation column 7 is withdrawn via line 22, in order to withdraw low boilers and inerts from the apparatus (purge). This also avoids an accumulation which is hazardous to safety of low boilers, for example acetaldehyde.

In a preferred embodiment, the carboxylic ester which has not been converted in the reactive distillation column 7 is withdrawn by means of line 21 not from line 22, but from the upper rectification zone of the reactive distillation column 7.

The alcohol formed or released is preferably withdrawn at the upper rectification zone 15 of the distillation column 13 by means of lines 23 or 24. The advantage of withdrawing the alcohol via line 24 is that the distillate enriched with carboxylic ester of line 23 from the distillation column 13 can be recycled into the reactive distillation column 7 and fed in there preferably below the catalyst zone 8 and above the lower rectification zone 9 or in the upper third of the lower rectification zone 9. Recycling into the process by connecting line 23 to the first prereactor 1 and into the second prereactor 19 is likewise possible.

In order to prevent partial evaporation of the feed to a second prereactor 19, it is advantageous to allow the mixing of the aqueous carboxylic acid and the carboxylic ester-containing feed, and also the reaction in the second prereactor 19, to take place under elevated pressure. The elevated pressure required depends on the mixing ratio and the system composition, and preference is given to pressures in the range from 1 to 6 bar.

Figure 2:
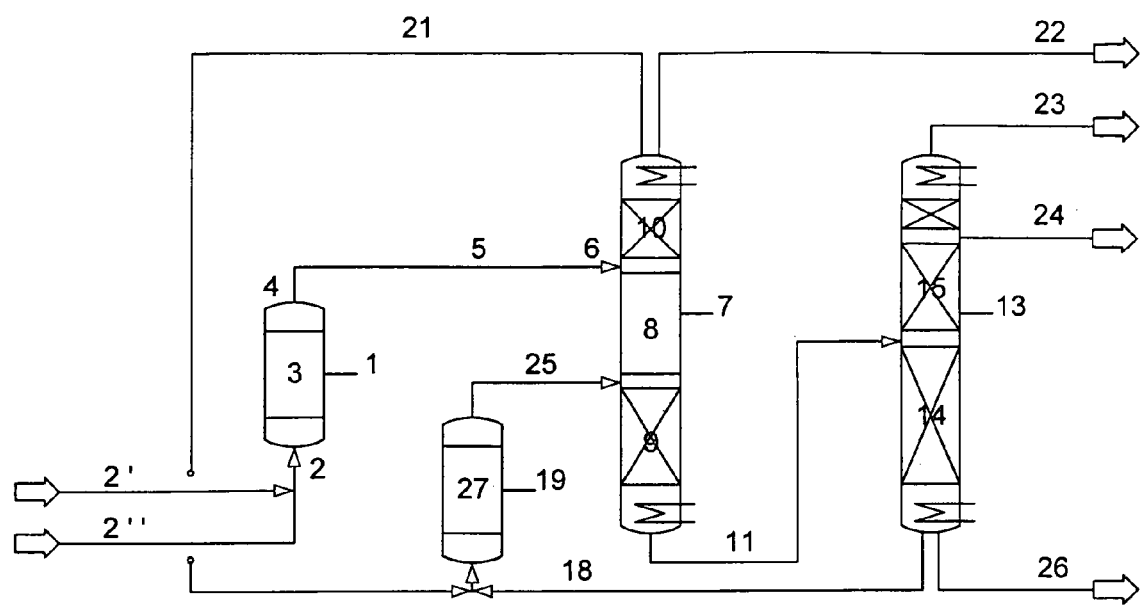
FIG. 2 illustrates a further embodiment of the present process and apparatus.

A second preferred embodiment of the inventive apparatus is reproduced in FIG. 2. The inventive apparatus according to drawing 2 differs from the inventive apparatus in FIG. 1 in that the line 21 is not connected to the feed of the carboxylic ester mixture to be hydrolyzed 2', to the water feed 2" or to the mixture 2, but rather to the line 18 which conducts the aqueous carboxylic acid from the bottom fraction of the distillation column 13 into the second prereactor 19. The feed 20 is accordingly dispensed with, and the line 21 may be connected to the line 22 or, in a further preferred embodiment, may be withdrawn from the upper rectification zone 10.

Figure 3:
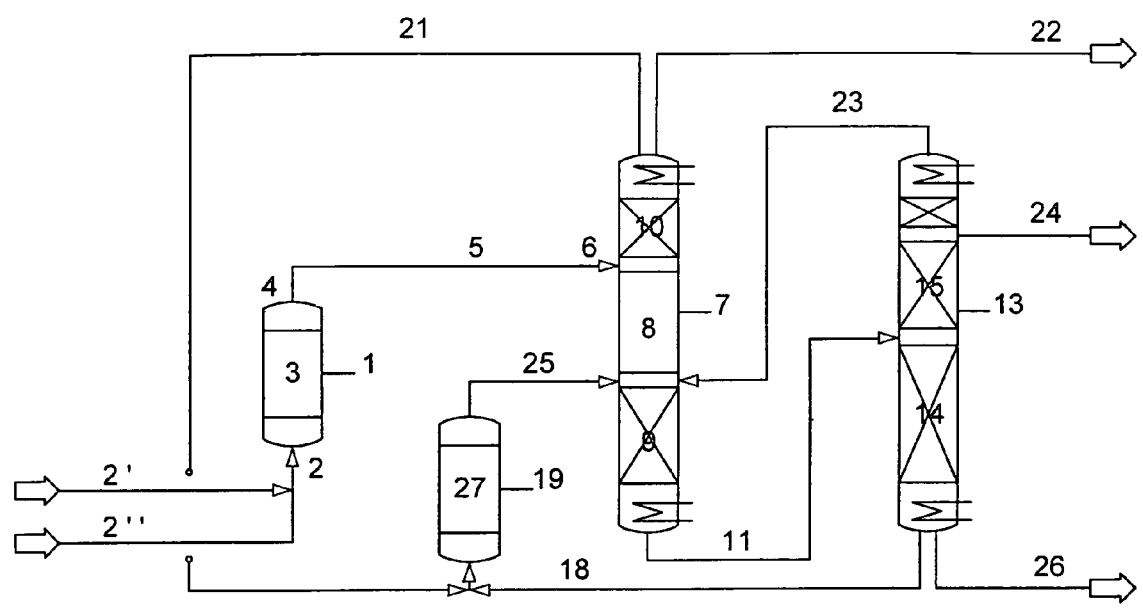
FIG. 3 illustrates a further embodiment of the present process and apparatus.

A further preferred embodiment of the inventive apparatus is reproduced in FIG. 3. This inventive apparatus differs from the inventive apparatus in FIG. 2 in that the line 23 for at least partial removal of the distillate from the distillation column 13 into the reactive distillation column 7 is connected to the latter. The line 23 is conducted into the reactive distillation column 7 preferably below the catalyst zone 8 and above the lower rectification zone 9 or in the upper third of the lower rectification zone 9.

Figure 4:
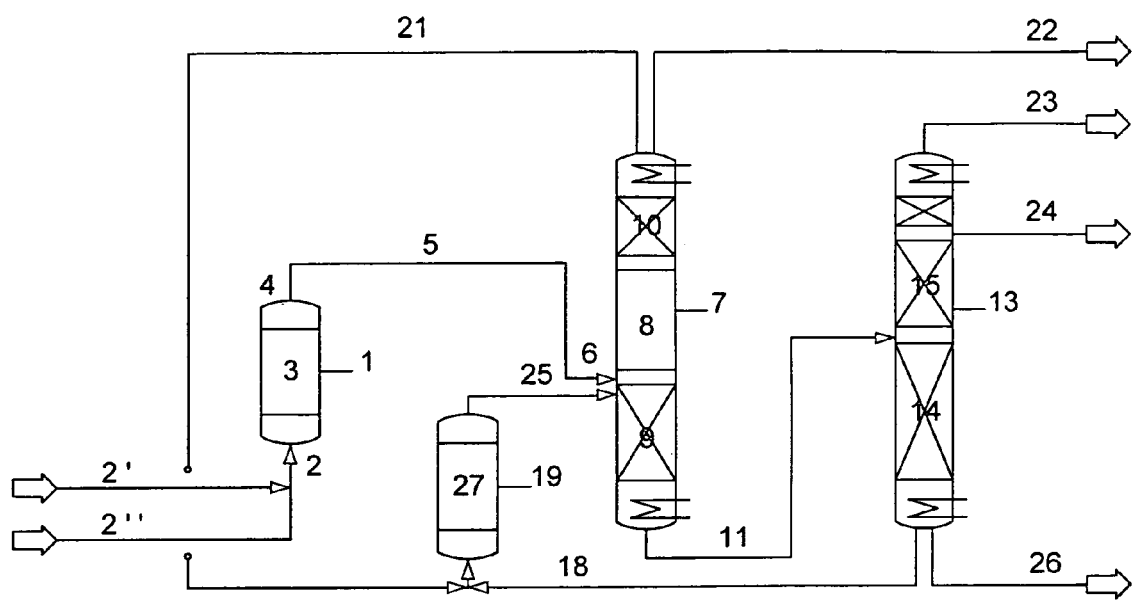
FIG. 4 illustrates a further embodiment of the present process and apparatus.
Figure 5:
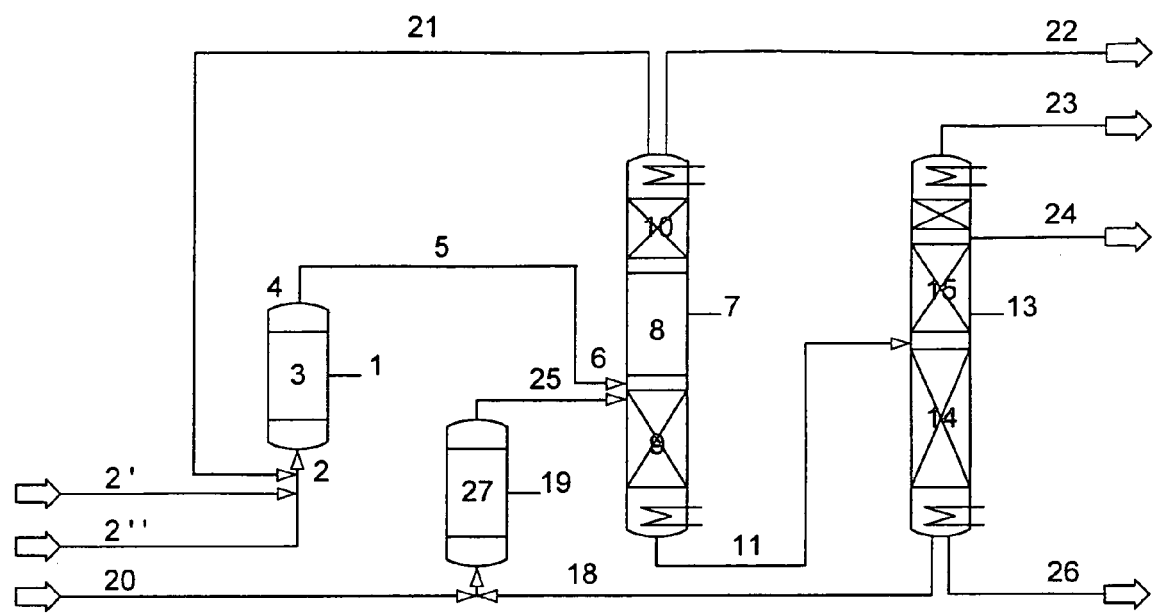
FIG. 5 illustrates a further embodiment of the present process and apparatus.

Further preferred embodiments for the hydrolysis of relatively high-boiling carboxylic esters having an increased water content in the low-boiling, usually ternary azeotrope are reproduced in FIGS. 4 and 5. These inventive apparatus differ from the inventive apparatus in FIGS. 2 and 1 in that the product of the first prereactor 1 is fed into the reactive distillation column 7 preferably below the reaction part 8 and above the rectification zone 9 or in the upper third of the lower rectification zone 9. The product of the second prereactor 19 is fed in below the reaction zone 8, preferably in the upper third of the lower rectification zone 9.

The process according to the invention can be used to hydrolyze preferably the carboxylic esters methyl and ethyl formate, methyl, ethyl, propyl, isobutyl and tert-butyl acetate, methyl and ethyl propionate, and also methyl, ethyl and propyl butyrate, in particular methyl acetate.

An inventive process and also an inventive apparatus for hydrolyzing a carboxylic ester is now to be described by way of example using the acid-catalyzed hydrolysis of methyl acetate. A fluid stream comprising the azeotrope of methyl acetate and methanol, corresponding to a molar ratio of 1.94:1, from polyvinyl alcohol production, is mixed with an at least equimolar amount of water, preferably a 4- to 7-fold molar excess of water, based on methyl acetate. The water used is hot water which heats the mixture to a temperature between 50 and 80° C. The mixture is passed into the first prereactor 1 which is preferably arranged vertically.

The first prereactor 1 is packed with a cationic ion exchanger as an acidic solid catalyst. The catalyst preferably has a particle size between about 0.35 and 3 mm. Such a catalyst material is obtainable, for example, under the name Amberlyst 15® from Rohm & Haas. Alternative catalysts are, for example, zeolites, alumina, silica, etc.

The mixture of methyl acetate and water flows through the first prereactor 1 and is contacted with the catalyst material. This results in partial hydrolysis of the methyl acetate. The conversion of the methyl acetate in the first prereactor 1 is between 20 and 100%, preferably between 60 and 100%, of the equilibrium conversion. The resulting reaction mixture is introduced via line 5, preferably above the catalyst zone 8 and below the rectification zone 10 of the reactive distillation column 7.

The reactive distillation column 7 is preferably operated in such a way that the two hydrolysis products, methanol and acetic acid, are removed from the bottom fraction together with the unconverted water. The remaining, volatile methyl acetate is removed from the reaction products in the lower rectification zone 9 and concentrated distillatively in the catalyst zone 8 for hydrolysis. The reaction products formed, methanol and acetic acid, are permanently discharged distillatively from the catalyst zone 8 into the lower rectification zone 9 or into the bottom fraction, line 11.

The mixture of acetic acid, water and methanol which is obtained in the bottom fraction of the reactive distillation column 7 is further separated in the downstream distillation column 13, in which methanol is removed at the top of the column or at the upper distillation zone 15 and the mixture of acetic acid and water is obtained in the bottom fraction of the distillation column 13. This aqueous acetic acid is removed via line 26 and at least partly fed via line 18 into the second prereactor 19. Alternatively, the recycling amount of aqueous carboxylic acid can be withdrawn by means of a sidestream takeoff of the lower rectification zone 14, preferably from its lower half.

Before entry into the second prereactor 19 via line 20, further methyl acetate is fed to line 18. In a further preferred embodiment, a methyl acetate stream is fed in via line 20 and preferably contains from 50 to 100%, more preferably from 90 to 100%, methyl acetate. This methyl acetate stream is, for example, supplied from methyl acetate which has already been further purified and is obtained, for example, from polyvinyl alcohol production. The aqueous acetic acid from the bottom fraction of the distillation column 13 has a temperature higher than 30° C., preferably from 50 to 110° C., more preferably from 100 to 105° C. The mixing with the methyl acetate heats the inlet stream of the second prereactor 19 already to temperatures of from 25 to 100° C., preferably to from 50 to 90° C., more preferably to from 70 to 90° C. The mixing of the feeds and the reaction in the second reactor proceeds as a consequence of the high vapor pressure of methyl acetate, preferably under elevated pressure.

The second prereactor 19 preferably has an acidic solid catalyst. The second prereactor 19 is preferably flowed through from bottom to top and is operated at a preferred temperature of from 50 to 120° C., more preferably from 70 to 90° C. The conversion of the methyl acetate is between 20 and 100%, preferably between 60 and 100%, of the equilibrium conversion. The outlet of the second prereactor 19 is connected to the reactive distillation column 7 by means of line 25. The line 25 is conducted into the reactive distillation column 7 preferably below the catalyst zone 8 and above the lower rectification zone 9 or in the upper third of the lower rectification zone 9.

In a further preferred inventive embodiment, the line 21 conducting distillate from the reactive distillation column 7, optionally containing unconverted methyl acetate, is fed to line 18. The line 20 is accordingly dispensed with. This embodiment has the advantage that unconverted methyl acetate is fed to the hydrolysis in the second prereactor 19 and optionally to the reactive distillation column 7.

The temperature in the first prereactor 1, second prereactor 19 and in the reactive distillation column 7 is determined as a function of pressure, and a certain elevated pressure allows a higher temperature and therefore a higher reaction rate and a more favorable equilibrium position. Preference is given to operating the apparatus or parts of the apparatus at elevated pressures of from 1 to 6 bar, more preferably from 1.5 to 3 bar.

Deviating from the design of a plant in accordance with the prior art, where process feed having a molar ratio of methyl acetate to methanol of 1.94:1 corresponding to the azeotrope is introduced into the process, this, as a consequence of the shifting of the equilibrium reaction at the expense of the products, reduces the maximum available capacity of a plant according to the prior art. The increased recycling of methyl acetate-rich distillate from the reactive distillation column 7 to the first prereactor 1 and the very substantially fixed geometry of the catalyst zone 8 of the reactive distillation column 7 restricts the extent of a capacity increase using the existing structure.

An azeotrope of methyl acetate and methanol is not preferred as a feed for the second prereactor 19, since the alcohol content thus fed in shifts the equilibrium reaction of the acidic hydrolysis unfavourably for the products. As already mentioned, the molar ratio of methyl acetate to methanol in the azeotrope is 1.94:1. In the top fraction having a high methyl acetate content and in the distillate of the reactive distillation column 7, the ratio is about 4:1 or higher, which is considerably more favorable for the conversion. It is therefore particularly advantageous to introduce the distillate of the reactive distillation column 7 into the second prereactor 19, instead of feeding it to the feed of the first prereactor 1. In addition, a decrease in the distillate from the upper rectification zone 10 of the reactive distillation column 7 favors the conversion as a result of the lower content of low boilers to be discharged and the water content rising toward the catalyst zone 8. A ratio of only 1:1 is suitable for converting about 33% of the methyl acetate fed which is diluted by approx. 35% by weight of acetic acid. This means that the amount of distillate fed, line 21, to the reactive distillation column 7 can be used to optimize the methyl acetate conversion. This equally applies to the recycled aqueous carboxylic acid stream, line 18. An increased inlet stream of azeotrope of metyl acetate and methanol to the first prereactor 1 replaces the amount of distillate which is no longer present, line 21, of the reactive distillation column 7 and thus allows the capacity increase.

The high exit temperature of the aqueous acetic acid at the stripping section of the distillation column 13 of preferably from 100 to 105° C. enables a mixing temperature with the methyl acetate in the order of magnitude from 70 to 90° C., which favors the hydrolysis of the methyl acetate fed in the second prereactor 19. Particular preference is given to process operation under slightly elevated pressure of from 1.5 to 3 bar. The operation under elevated pressure can be taken into account simply by suitable pipeline control.

The recycling of dilute acid to a second prereactor 19 and the feeding into the reactive distillation 7 leads to a distinctly increased fluid dynamic loading of the stripping sections (9, 10) of the reactive distillation column 7 and the optional downstream distillation column 13.

The capacity of a prior art plant can be estimated at an additional 80 to 100% by introducing a second prereactor 19 and recycling the aqueous carboxylic acid, and the specific heating vapor requirements of the plant only increases slightly.

The incorporation of the second prereactor 19 is simple from the point of view of installation and process technology. The embodiment which is preferred in accordance with the invention likewise allows more highly concentrated aqueous acetic acid to be produced by not increasing the water feed to the first prereactor 1 proportionally to the amount of methyl acetate.

In the experimental examples which follow, the catalyst used is a commercial cationic solid catalyst. In the reactive distillation column 7 the catalyst was installed in a structured catalyst packing.

EXAMPLE 1

COMPARATIVE EXAMPLE

A combination of the prereactor 1 with reactive distillation column 7 was used. There was no recycling of distillate from the reactive distillation column 7 to the prereactor 1 by means of line 21. The methyl acetate stream to be hydrolyzed had approximately the azeotropic composition of 81% by weight of methyl acetate and 19% by weight of methanol. The bottom fraction of the reactive distillation column 7 comprises methanol, acetic acid, water and traces of methyl acetate. This mixture was separated in the distillation column 13 into a methanol stream comprising traces of methyl acetate and into an acetic acid/water mixture.

| Reactive distillation column 7: | |
|---|---|
| Diameter: | 1100 mm |
| Upper rectification zone 10: | 5 theoretical plates |
| Catalyst zone 8: | 3 theoretical plates |
| Lower rectification zone 9: | 8 theoretical plates |
| Feed streams: | |
| Azeotrope, line 2': | 700 kg/h |
| Water, line 2": | 900 kg/h |
| Product streams: | |
| Top fraction (purge), Line 22, of the reactive distillation column 7: | 26 kg/h |
| Bottom fraction, line 11, of the reactive distillation column 7: | 1574 kg/h |
| Experimental conditions: | |
| Top pressure of reactive distillation column 7: | 26 mbar gauge |
| Feed point of reactive distillation column 7: | above the catalyst zone 8 |
| Heating output of reactive distillation column 7: | 700 kW |
| Heating output of distillation column 13: | 490 kW |
| Entrance temperature to prereactor 1: | 58° C. |
| Result: | |
| Methyl acetate conversion in the prereactor 1: | 41.8% |
| Overall methyl acetate conversion: | 98.9% (neglecting the purge, line 22) |
| Composition of bottom fraction, line 11, of the reactive distillation column 7: | |
| Methyl acetate: | 0.4% by weight |
| Methanol: | 22.7% by weight |
| Water: | 49.6% by weight |
| Acetic acid: | 27.3% by weight |
| Composition of top fraction, line 23, of the distillation column 13: | |
| Methyl acetate: | 2.0% by weight |
| Methanol: | 98.0% by weight |
| Composition of bottom fraction, line 26, of the distillation column 13: | |
| Water: | 64.3% by weight |
| Acetic acid: | 35.7% by weight |

EXAMPLE 2

COMPARATIVE EXAMPLE—PROCESS WITH RECYCLING

A combination of the prereactor 1 with reactive distillation column 7 was used. There was recycling of distillate from the reactive distillation column 7 to the prereactor 1 by means of line 21. The methyl acetate stream to be hydrolyzed had approximately the azeotropic composition of 81% by weight of methyl acetate and 19% by weight of methanol. The bottom fraction of the reactive distillation column 7 comprises methanol, acetic acid, water and traces of methyl acetate. This mixture was separated in the distillation column 13 into a methanol stream comprising traces of methyl acetate and into an acetic acid/water mixture.

| Reactive distillation column 7: | |
|---|---|
| Diameter: | 1100 mm |
| Upper rectification zone 10: | 5 theoretical plates |
| Catalyst zone 8: | 3 theoretical plates |
| Lower rectification zone 9: | 8 theoretical plates |
| Feed streams: | |
| Azeotrope, line 2': | 685 kg/h |
| Water, line 2": | 930 kg/h |
| Product streams: | |
| Top fraction (purge), Line 22, of the reactive distillation column 7: | 15 kg/h |
| Bottom fraction, line 11, of the reactive distillation column 7: | 1600 kg/h |
| Experimental conditions: | |
| Top pressure of reactive distillation column 7: | 29 mbar gauge |
| Feed point of reactive distillation column 7: | above the catalyst zone 8 |
| Distillate recycling, line 21, to preactor 1: | 1985 kg/h |
| Heating output of reactive distillation column 7: | 490 kW |
| Heating output of distillation column 13: | 490 kW |
| Entrance temperature to prereactor 1: | 58° C. |
| Result: | |
| Methyl acetate conversion: | 99.1% (neglecting the purge, line 22) |
| Composition of bottom fraction, line 11, of the reactive distillation column 7: | |
| Methyl acetate: | 0.3% by weight |
| Methanol: | 22.7% by weight |
| Water: | 50.0% by weight |
| Acetic acid: | 27.4% by weight |
| Composition of top fraction, line 23, of the distillation column 13: | |
| Methyl acetate: | 1.5% by weight |
| Methanol: | 98.5% by weight |
| Composition of bottom fraction, line 26, of the distillation column 13: | |
| Water: | 64.6% by weight |
| Acetic acid: | 35.4% by weight |

EXAMPLE 3

A combination of two prereactors 1 and 19 having a reactive distillation column 7 according to FIG. 2 was used. The methyl acetate stream to be hydrolyzed had approximately the azeotropic composition of 81% by weight of methyl acetate and 19% by weight of methanol. The bottom fraction of the reactive distillation column 7 comprises methanol, acetic acid, water and traces of methyl acetate. This mixture was separated in the distillation column 13 into a methanol stream comprising traces of methyl acetate and into an acetic acid/water mixture.

| Reactive distillation column 7: | |
|---|---|
| Diameter: | 1100 mm |
| Upper rectification zone 10: | 5 theoretical plates |
| Catalyst zone 8: | 3 theoretical plates |
| Lower rectification zone 9: | 8 theoretical plates |
| Feed streams: | |
| Azeotrope, stream 2': | 1600 kg/h |
| Water, stream 2": | 2200 kg/h |
| Product streams: | |
| Top fraction (purge), Line 22, of the reactive distillation column 7: | 30 kg/h |
| Bottom stream, line 11, of the reactive distillation column 7: | 6170 kg/h |
| Distillate recycling, line 21, to second prereactor 19: | 3000 kg/h |
| Dilute acid recycling, line 18, to second prereactor 19: | 2400 kg/h |
| Top fraction, line 23, of the distillation column 13: | 870 kg/h |
| Bottom fraction, line 26, of the distillation column 13: | 2900 kg/h |
| Experimental conditions: | |
| Top pressure of the reactive distillation column 7: | 30 mbar gauge |
| Inlet 6 into reactive distillation column 7: | above the catalyst zone 8 |
| Inlet of the line 25 into reactive distillation column 7: | below the catalyst zone 8 |
| Heating output of reactive distillation column 7: | 1200 kW |
| Heating output of distillation column 13: | 1350 kW |
| Entrance temperature to prereactor 1: | 62° C. |
| Entrance temperature to prereactor 19: | 88° C. |
| Result: | |
| Methyl acetate conversion: | 98.8% neglecting the purge, line 22 |
| Composition of bottom fraction, line 11, of the reactive distillation column 7: | |
| Methyl acetate: | 0.3% by weight |
| Methanol: | 14.0% by weight |
| Water: | 55.7% by weight |
| Acetic acid: | 30.0% by weight |
| Composition of top fraction, line 23, of the distillation column 13: | |
| Methyl acetate: | 1.8% by weight |
| Methanol: | 98.2% by weight |
| Composition of bottom fraction, line 11, of the distillation column 13: | |
| Water: | 65.0% by weight |
| Acetic acid: | 35.0% by weight |

EXAMPLE 4

A combination of two prereactors 1 and 19 having a reactive distillation column 7 according to FIG. 3 was used. The feed of methyl acetate was increased and the water excess reduced. The methyl acetate stream to be hydrolyzed had approximately the azeotropic composition of 81% by weight of methyl acetate and 19% by weight of methanol. The bottom fraction of the reactive distillation column 7 comprises methanol, acetic acid, water and traces of methyl acetate. This mixture was separated in the distillation column 13 into a methanol stream comprising traces of methyl acetate and into an acetic acid/water mixture.

| Reactive distillation column 7: | |
|---|---|
| Diameter: | 1100 mm |
| Upper rectification zone 10: | 5 theoretical plates |
| Catalyst zone 8: | 3 theoretical plates |
| Lower rectification zone 9: | 8 theoretical plates |
| Feed streams: | |
| Azeotrope, line 2': | 1700 kg/h |
| Water, line 2": | 1700 kg/h |
| Product streams: | |
| Top fraction (purge), Line 22, of the reactive distillation column 7: | 35 kg/h |
| Bottom fraction, line 11, of the reactive distillation column 7: | 6865 kg/h |
| Distillate recycling, line 21, to second prereactor 19: | 3500 kg/h |
| Dilute acid recycling, Line 18, to second prereactor 19: | 3500 kg/h |
| Distillate, line 23, of the distillation column 13: | 930 kg/h |
| Bottom fraction, line 26, of the distillation column 13: | 2435 kg/h |
| Experimental conditions: | |
| Top pressure of the reactive distillation column 7: | 37 mbar |
| Inlet 6 into reactive distillation column 7: | above the catalyst zone 8 (neglecting the purge, line 22) |
| Inlet of the line 25 into reactive distillation column 7: | below the catalyst zone 8 |
| Heating output of reactive distillation column 7: | 1300 kW |
| Heating output of distillation column 13: | 1300 kW |
| Entrance tempreature to prereactor 1: | 65° C. |
| Entrance temperature to prereactor 19: | 77° C. |

-continued

| Result: | |
|---|---|
| Methyl acetate conversion: | 98.2% |
| Composition of bottom fraction, line 11, of the reactive distillation column 7: | |
| Methyl acetate: | 0.4% by weight |
| Methanol: | 13.3% by weight |
| Water: | 48.4% by weight |
| Acetic acid: | 37.9% by weight |
| Composition of top fraction, line 23, of the distillation column 13: | |
| Methyl acetate: | 2.7% by weight |
| Methanol: | 97.3% by weight |
| Composition of bottom fraction, line 26, of the distillation column 13: | |
| Water: | 56.1% by weight |
| Acetic acid: | 43.9% by weight |

EXAMPLE 5

As a further inventive example, the hydrolysis of isobutyl acetate to isobutanol and acetic acid is considered by means of process simulation. Isobutyl acetate was selected because its normal boiling point within the group of isobutyl acetate, isobutanol, acetic acid and water is the highest. The boiling points of the two reaction products, isobutanol and acetic acid, are above that of the reaction partner water.

| Normal boiling points: | |
|---|---|
| Isobutyl acetate (iBuAc): | 117.2° C. |
| Water (H$_2$O): | 100.0° C. |
| Isobutanol (iBuOH): | 107.9° C. |
| Acetic acid (AA): | 117.9° C. |

Binary Azeotropes:

77.7% by weight of isobutyl acetate, 22.3% by weight of water; normal boiling point: 88.4° C.

44.9% by weight of isobutyl acetate, 55.1% by weight of isobutanol;

normal boiling point: 105.1° C.

66.8% by weight of isobutanol, 33.2% by weight of water; normal boiling point: 89.9° C.

Ternary Azeotrope 46.5% by weight of isobutyl acetate, 30.4% by weight of water, 23.1% by weight of isobutanol; normal boiling point: 86.8° C.

52.3% by weight of isobutyl acetate, 21.3% by weight of water, 26.4% by weight of isobutanol, normal boiling point: 86.6° C.

The process was carried out on the basis of equilibrium calculations with respect to the mass transfer and the chemical conversion. The dimerization of the carboxylic acid was taken into account by the approach of Hayden O'Connel. For the description of the chemical equilibrium, the equilibrium constant according to formula (1)

$$K_x = (x(iBuOH) * x(AA))/(x(iBuAc) * x(H_2O)) = 0.05 \text{ mol}^2/\text{mol}^2 \tag{1}$$

was used.

The process configuration selected is illustrated in FIG. 5. It is based on FIG. 1, except that the feed points to the reactive distillation column 7 were adapted to the boiling conditions of the system.

| Reactive distillation column 7: | |
|---|---|
| Upper rectification zone 10: | stage 1 to 4; 4 theoretical plates |
| Catalyst zone 8: | stage 5 to 7; 3 theoretical plates |
| lower rectification zone 9: | stage 8 to 23; 16 theoretical plates |
| Reflux ratio: | 1.12 |
| Feed to the first prereactor 1: | above stage 8; below catalyst zone 8 |
| Feed to second prereactor 19: | above stage 11; in the upper third of the lower rectification zone 9 |
| First prereactor 1: | Temperature: 100° C. Pressure: 1 bar gauge Chemical equilibrium |
| Second prereactor 19: | Temperature: 100° C. Pressure: 1 bar gauge Chemical equilibrium |
| Distillation column 13: | 28 separating stages Reflux ratio: 2.5 |
| Connection: | Line 21 branches off from line 22 Line 18 branches off from line 26 |

Feed and Product Streams:

| | Line | | | | | | | | | | |
|---|---|---|---|---|---|---|---|---|---|---|---|
| | 2' | 2'' | 20 | 5 | 11 | 18 | 21 | 22 | 23 | 25 | 26 |
| Flow rate (kg/h) | 1000 | 1980 | 350 | 8914 | 8264 | 5000 | 5934 | 66 | 1400 | 5350 | 1864 |
| H$_2$0 (% by wt.) | | 100 | | 37.0 | 60.6 | 64.8 | 24.7 | 24.7 | 39.9 | 60.4 | 64.8 |
| iBuAc (% by wt.) | 97.0 | | 97.0 | 33.1 | 0.01 | | 48.7 | 48.7 | 0.09 | 5.1 | |
| AA (% by wt.) | | | | 5.3 | 29.2 | 35.2 | | | | 33.5 | 35.2 |
| iBuOH (% by wt.) | 3.0 | | 3.0 | 24.6 | 10.1 | | 26.6 | 26.6 | 60.1 | 1.0 | |

The comparison of the simulation of the hydrolysis of isobutyl acetate by means of a connection of the prereactor 1 to the reactive distillation column 7 and the recycling of equal amounts of distillate by means of line 21 at the same heating output and the same water excess, line 2", shows that only the proceed feed 2' of 1000 kg/h can be converted. The inventive incorporation of the second prereactor 19 thus allows the process flow rate of 1350 kg/h to be hydrolyzed. This corresponds to a capacity increase of 35%.

What is claimed is:

1. A process for acid-catalyzed hydrolysis of a carboxylic ester to the corresponding carboxylic acid and alcohol hydrolysis products in the presence of water, comprising
    introducing carboxylic ester and water into a first prereactor containing a hydrolysis catalyst which hydrolyzes the carboxylic ester at least partly to hydrolysis products,
    removing a reaction mixture from the first prereactor and introducing at least a portion thereof into a reactive distillation column containing a hydrolysis catalyst which further converts a water-containing carboxylic ester stream to carboxylic acid and alcohol, and simultaneously at least partly separating the water-containing carboxylic ester stream into components thereof, mixture(s) comprising compounds of low volatility and low-boiling carboxylic ester being removed at least partly as a distillate from an upper rectification zone of the reactive distillation column and/or an accompanying condensation system, and
    collecting less volatile compounds at least partly as a bottom fraction from the reactive distillation column which is passed into a further distillation column, wherein aqueous carboxylic acid from the bottom fraction or from the lower rectification zone of the distillation column is mixed with further carboxylic ester and directed to a second prereactor containing a hydrolysis catalyst, and a reaction mixture is removed from the second prereactor and passed at least partly into the reactive distillation column.

2. The process of claim 1, wherein aqueous carboxylic acid from the bottom fraction or from the lower rectification zone of the distillation column is mixed with a separately fed carboxylic ester stream or carboxylic ester-containing stream and fed to the second prereactor.

3. The process of claim 1, wherein a distillate of the reactive distillation column comprising carboxylic ester which is yet to be converted to hydrolysis products is fed at least partly back to the first prereactor.

4. The process of claim 1, wherein aqueous carboxylic acid from the bottom fraction or from the lower rectification zone of the distillation column is mixed with distillate of the reactive distillation column comprising carboxylic ester which is yet to be converted to hydrolysis products, and the resulting mixture is subsequently fed to the second prereactor.

5. The process of claim 1, wherein an aqueous, hot carboxylic acid stream from the bottom fraction or from the lower rectification zone of the distillation column is utilized for heating the stream comprising carboxylic ester to be mixed therewith.

6. The process of claim 1, wherein the reaction product from the second prereactor is fed in below the reaction zone and above the lower rectification zone or in the upper third of the lower rectification zone of the reactive distillation column.

7. The process of claim 1, wherein carboxylic ester is selected from the group consisting of methyl and ethyl formate, methyl, ethyl, propyl, isobutyl and tert-butyl acetate, methyl and ethyl propionate and methyl, ethyl and propyl butyrate.

8. The process of claim 1, wherein the inlet stream to the first prereactor comprises an azeotrope of the carboxylic ester with the corresponding alcohol.

9. The process of claim 1, wherein low boilers are at least partly removed from the distillate of the reactive distillation column.

10. The process of claim 1, which is operated continuously.

* * * * *